(12) United States Patent
Reunanen et al.

(10) Patent No.: US 11,168,058 B2
(45) Date of Patent: Nov. 9, 2021

(54) MANUFACTURE OF A CRYSTALLINE PHARMACEUTICAL PRODUCT

(71) Applicant: ORION CORPORATION, Espoo (FI)

(72) Inventors: Merja Reunanen, Espoo (FI); Anna Staffans, Espoo (FI)

(73) Assignee: ORION CORPORATION, Espoo (FI)

( * ) Notice: Subject to any disclaimer, the term of this patent is extended or adjusted under 35 U.S.C. 154(b) by 0 days.

(21) Appl. No.: 16/491,642

(22) PCT Filed: Feb. 27, 2018

(86) PCT No.: PCT/FI2018/050143
§ 371 (c)(1),
(2) Date: Sep. 6, 2019

(87) PCT Pub. No.: WO2018/162793
PCT Pub. Date: Sep. 13, 2018

(65) Prior Publication Data
US 2020/0039940 A1     Feb. 6, 2020

(30) Foreign Application Priority Data
Mar. 7, 2017   (FI) ...................................... 20175202

(51) Int. Cl.
*C07D 231/14*       (2006.01)
*A61K 45/06*        (2006.01)

(52) U.S. Cl.
CPC ............ *C07D 231/14* (2013.01); *A61K 45/06* (2013.01)

(58) Field of Classification Search
CPC ......................... C07D 231/14; A61K 31/4155
See application file for complete search history.

(56) References Cited

U.S. PATENT DOCUMENTS 8,921,378 B2   12/2014   Tormakangas et al.
8,975,254 B2   3/2015    Wohlfahrt et al.

FOREIGN PATENT DOCUMENTS

WO   WO 2012/143599 A1   10/2012
WO   WO 2016/120530 A1   8/2016

OTHER PUBLICATIONS

Caira, Crystalline Polymorphism of Organic Compounds, Topics in Current Chemistry, 1999, vol. 198, p. 164-208. (Year: 1999).*
International Search Report, issued by the European Patent Office in International Application No. PCT/2018/050143, dated Apr. 20, 2018 (2 pages).
Annex 1. Comparative crystallization experiments between particles of the invention and particles of D1 (WO 2016/120530) (1 page).
Third Party Observation for Application No. EP20180709661 dated Mar. 12, 2021 (4 pages).

* cited by examiner

*Primary Examiner* — Karen Cheng
(74) *Attorney, Agent, or Firm* — Finnegan, Henderson, Farabow, Garrett & Dunner, LLP

(57) ABSTRACT

The present disclosure relates to crystalline particles of N—((S)-1-(3-(3-chloro-4-cyanophenyl)-1H-pyrazol-1-yl)-propan-2-yl)-5-(1-hydroxyethyl)-1H-pyrazole-3-carboxamide (I) having specific surface area (SSA) in the range from about 8 to about 16 m$^2$/g, preferably from about 10 to about 15 m$^2$/g, and to the method for the preparation of such particles. Compound (I) is a potent androgen receptor (AR) modulator which is useful as a medicament for example in the treatment of prostate cancer.

29 Claims, 2 Drawing Sheets

MANUFACTURE OF A CRYSTALLINE PHARMACEUTICAL PRODUCT

This is a National Stage Application under 35 U.S.C. § 371 of International Patent Application No. PCT/FI2018/050143, filed Feb. 27, 2018, which claims the benefit of Finnish Patent Application No. 20175202, filed Mar. 7, 2017, both of which are incorporated herein by reference.

FIELD OF THE INVENTION

The present invention relates to crystalline particles of N—((S)-1-(3-(3-chloro-4-cyanophenyl)-1H-pyrazol-1-yl)-propan-2-yl)-5-(1-hydroxyethyl)-1H-pyrazole-3-carboxamide (I) having specific surface area (SSA) in the range from about 8 to about 16 m²/g, preferably from about 10 to about 15 m²/g, and to the method for the preparation of such particles.

BACKGROUND OF THE INVENTION

The compound N—((S)-1-(3-(3-chloro-4-cyanophenyl)-1H-pyrazol-1-yl)-propan-2-yl)-5-(1-hydroxyethyl)-1H-pyrazole-3-carboxamide (I) and manufacture thereof have been disclosed in WO 2011/051540. Compound (I) is a potent androgen receptor (AR) modulator useful in the treatment of cancer, particularly AR dependent cancer such as prostate cancer, and other diseases where AR antagonism is desired. Compound (I) is represented by the structure:

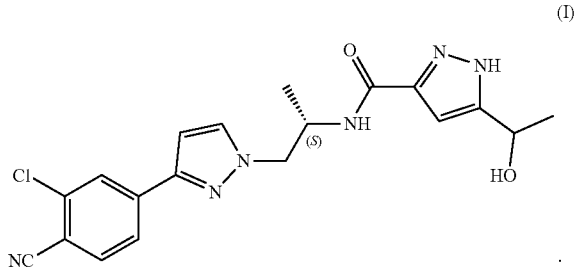

(I)

As the hydrogen atom of the pyrazole ring may exist in tautomeric equilibrium between the 1- and 2-position, it is recognized by the skilled person that the above structure and the chemical name "N—((S)-1-(3-(3-chloro-4-cyanophenyl)-1H-pyrazol-1-yl)-propan-2-yl)-5-(1-hydroxyethyl)-1H-pyrazole-3-carboxamide (I)," as referred to herein, is inclusive of the tautomer of compound (I), namely N—((S)-1-(3-(3-chloro-4-cyanophenyl)-1H-pyrazol-1-yl)-propan-2-yl)-3-(1-hydroxyethyl)-1H-pyrazole-5-carboxamide.

Compound (I) is poorly soluble in water. Poorly soluble compounds often suffer from low oral bioavailability. Enhancement of bioavailability of poorly soluble drugs is routinely attempted by micronization. Micronization, i.e. reduction of particle size to the range of only few micrometers, typically increases the dissolution rate of the poorly soluble drug through increased specific surface area (SSA). Micronized particles, however, often suffer from poor flow and dispersion properties causing drawbacks in subsequent pharmaceutical processing.

A stable crystalline form of compound (I) and a method for the preparation thereof by crystallization from a mixture of acetonitrile and water has been disclosed in WO 2016/120530. The method produces small irregular particles with sharp edges. Such particles are not optimal for pharmaceutical processing purposes either, for example due to poor flowability of the powder or cumbersome isolation. Therefore, there is a need for crystalline particles of compound (I) which are better suited for pharmaceutical processing.

SUMMARY OF THE INVENTION

It has now been found that compound (I) can be obtained from the crystallization solvent as crystalline particles which have better properties for subsequent pharmaceutical processing. In one aspect, the obtained particles have consistent and relatively high specific surface area (SSA) in the range of 8-16 m²/g, preferably in the range of 10-15 m²/g, large volume median diameter, for example in the range of 100-1000 µm, and narrow particle size distribution. In another aspect, the particles have rounded particle shape. The particles having rounded particle shape are characterized by substantial lack of sharp edges. The particles of the present invention are easy to isolate, free flowing and exhibit reduced stickiness. Moreover, it was found that the specific surface area (SSA) of the particles in the range of from about 8 to about 16 m²/g, preferably from about 10 to about 15 m²/g, does not significantly change even though the volume median diameter of the particles is reduced to the range of 10-100 µm, e.g. by milling. This ascertains consistent bioavailability regardless of the variability in particle size.

Therefore the particles according to the present invention are particularly well suited for pharmaceutical processing.

Thus, according to one aspect, the present invention provides crystalline particles of N—((S)-1-(3-(3-chloro-4-cyanophenyl)-1H-pyrazol-1-yl)-propan-2-yl)-5-(1-hydroxyethyl)-1H-pyrazole-3-carboxamide (I) having specific surface area (SSA) in the range from about 8 to about 16 m²/g, preferably from about 10 to about 15 m²/g.

According to another aspect, the present invention provides crystalline particles of N-((S)-1-(3-(3-chloro-4-cyanophenyl)-1H-pyrazol-1-yl)-propan-2-yl)-5-(1-hydroxyethyl)-1H-pyrazole-3-carboxamide (I) having specific surface area (SSA) in the range from about 8 to about 16 m²/g, preferably from about 10 to about 15 m²/g, and a volume median diameter (Dv50)≥10 µm, preferably ≥15 µm, more preferably ≥20 µm.

According to another aspect, the present invention provides crystalline particles of N—((S)-1-(3-(3-chloro-4-cyanophenyl)-1H-pyrazol-1-yl)-propan-2-yl)-5-(1-hydroxyethyl)-1H-pyrazole-3-carboxamide (I) having specific surface area (SSA) in the range from about 8 to about 16 m²/g, preferably from about 10 to about 15 m²/g, and a volume median diameter (Dv50) between 10-1000 µm, preferably between 15-800 µm, more preferably between 20-750 µm.

According to another aspect, the present invention provides crystalline particles of N-((S)-1-(3-(3-chloro-4-cyanophenyl)-1H-pyrazol-1-yl)-propan-2-yl)-5-(1-hydroxyethyl)-1H-pyrazole-3-carboxamide (I) having specific surface area (SSA) in the range from about 8 to about 16 m²/g, preferably from about 10 to about 15 m²/g, and a volume median diameter (Dv50) between 100-1000 µm, preferably between 120-800 µm, more preferably between 150-750 µm. According to one particular aspect of the above embodiment of the invention, the crystalline particles have rounded particle shape.

According to still another aspect, the present invention provides crystalline particles of N—((S)-1-(3-(3-chloro-4-cyanophenyl)-1H-pyrazol-1-yl)-propan-2-yl)-5-(1-hydroxyethyl)-1H-pyrazole-3-carboxamide (I) having volume median diameter (Dv50) between 100-1000 μm, preferably between 120-800 μm, more preferably between 150-750 μm, and rounded particle shape.

According to still another aspect, the present invention provides a pharmaceutical dosage form comprising N—((S)-1-(3-(3-chloro-4-cyanophenyl)-1H-pyrazol-1-yl)-propan-2-yl)-5-(1-hydroxyethyl)-1H-pyrazole-3-carboxamide (I) as an active ingredient, wherein the active ingredient is in the form of crystalline particles according to any of the above embodiments.

According to still another aspect, the present invention provides a pharmaceutical dosage form, wherein the active ingredient is prepared from crystalline particles of N—((S)-1-(3-(3-chloro-4-cyanophenyl)-1H-pyrazol-1-yl)-propan-2-yl)-5-(1-hydroxy-ethyl)-1H-pyrazole-3-carboxamide (I) having volume median diameter (Dv50) between 100-1000 μm and rounded particle shape, for example by milling said particles to provide volume median diameter (Dv50) between 10-100 μm.

According to still another aspect, the present invention provides a pharmaceutical dosage form, wherein the active ingredient is prepared from crystalline particles of N-((S)-1-(3-(3-chloro-4-cyanophenyl)-1H-pyrazol-1-yl)-propan-2-yl)-5-(1-hydroxy-ethyl)-1H-pyrazole-3-carboxamide (I) having specific surface area (SSA) in the range from about 8 to about 16 $m^2/g$, preferably from about 10 to about 15 $m^2/g$, volume median diameter (Dv50) between 100-1000 μm and rounded particle shape, for example by milling said particles to provide volume median diameter (Dv50) between 10-100 μm.

According to still another aspect, the present invention provides a method for preparing crystalline particles of N—((S)-1-(3-(3-chloro-4-cyanophenyl)-1H-pyrazol-1-yl)-propan-2-yl)-5-(1-hydroxyethyl)-1H-pyrazole-3-carboxamide (I), the method comprising the steps of a) providing N—((S)-1-(3-(3-chloro-4-cyanophenyl)-1H-pyrazol-1-yl)-propan-2-yl)-5-(1-hydroxyethyl)-1H-pyrazole-3-carboxamide (I) in a solvent which comprises ethanol and water, wherein the amount of water is 35-60%, preferably 40-58%, more preferably 42-55%, per weight of the solvent;

b) heating the mixture to about refluxing temperature until N—((S)-1-(3-(3-chloro-4-cyanophenyl)-1H-pyrazol-1-yl)-propan-2-yl)-5-(1-hydroxyethyl)-1H-pyrazole-3-carboxamide (I) has dissolved;

c) cooling the mixture to about 20-35° C. during at least 3 hours, preferably during about 4 to about 8 hours, optionally with seeding;

d) adding, optionally simultaneously with step c), water during at least 1 hour, preferably during about 2 to about 10 hours, such that after step d) the amount of water in the solvent is 55-80%, preferably 58-78%, more preferably 60-75%, per weight of said solvent; and e) isolating the precipitate.

According to still another aspect, the present invention provides crystalline particles of N—((S)-1-(3-(3-chloro-4-cyanophenyl)-1H-pyrazol-1-yl)-propan-2-yl)-5-(1-hydroxy-ethyl)-1H-pyrazole-3-carboxamide (I) having volume median diameter (Dv50) between 100-1000 μm, preferably between 120-800 μm, more preferably between 150-750 μm, and having rounded particle shape, said particles being obtainable by a method comprising the steps of a) providing N—((S)-1-(3-(3-chloro-4-cyanophenyl)-1H-pyrazol-1-yl)-propan-2-yl)-5-(1-hydroxyethyl)-1H-pyrazole-3-carboxamide (I) in a solvent which comprises ethanol and water, wherein the amount of water is 35-60%, preferably 40-58%, more preferably 42-55%, per weight of the solvent;

b) heating the mixture to about refluxing temperature until N—((S)-1-(3-(3-chloro-4-cyanophenyl)-1H-pyrazol-1-yl)-propan-2-yl)-5-(1-hydroxyethyl)-1H-pyrazole-3-carboxamide (I) has dissolved;

c) cooling the mixture to about 20-35° C. during at least 3 hours, preferably during about 4 to about 8 hours, optionally with seeding;

d) adding, optionally simultaneously with step c), water during at least 1 hour, preferably during about 2 to about 10 hours, such that after step d) the amount of water in the solvent is 55-80%, preferably 58-78%, more preferably 60-75%, per weight of said solvent; and e) isolating the precipitate.

According to one particular embodiment, particles being obtainable by the above method have specific surface area (SSA) in the range from about 8 to about 16 $m^2/g$, preferably from about 10 to about 15 $m^2/g$.

DETAILED DESCRIPTION OF THE INVENTION

Figure 1:
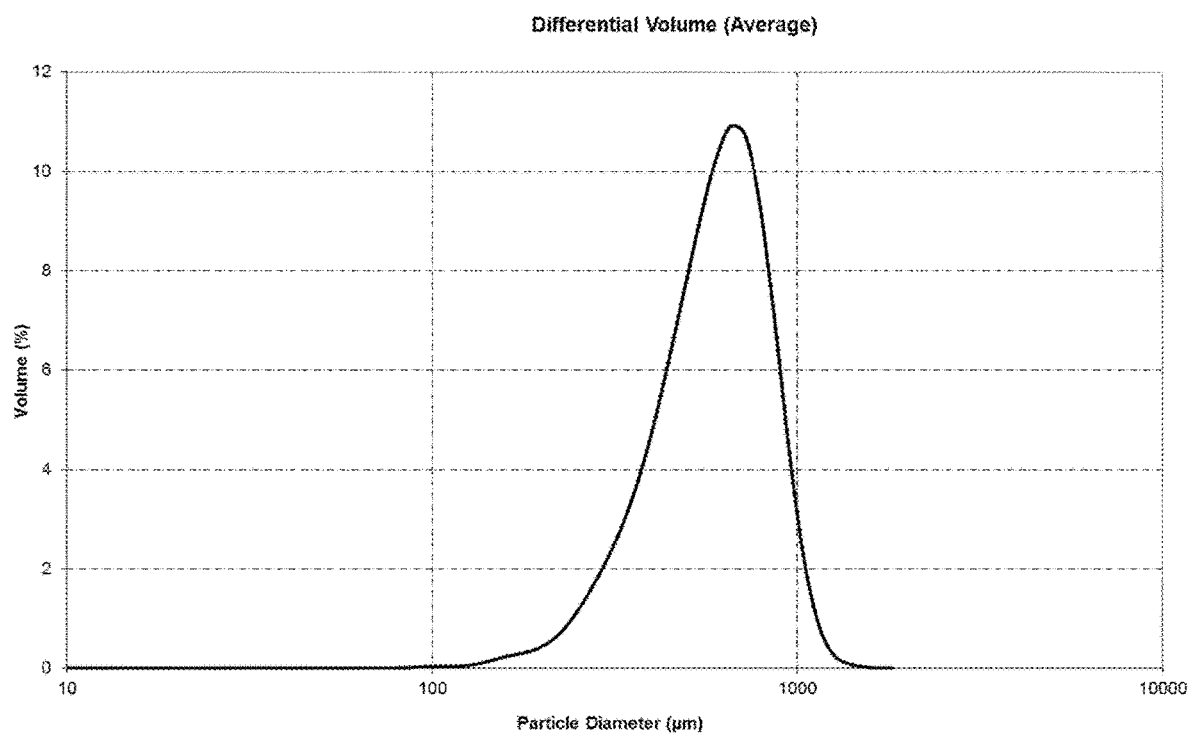
FIG. 1 shows particle size distribution of crystalline particles of compound (I) prepared according to the present invention as analyzed by laser light diffraction.

The term "particles having rounded particle shape", as used herein, refers to particles according to the present invention having substantially spherical, elliptical or potato-like geometries with curved surfaces substantially lacking sharp or rough edges, such geometries and surfaces being consistent and apparent when the particles are examined under a scanning electron microscope, particularly with 50-100 fold magnification. The rounded particles according to the invention are further characterized by having mean aspect ratio higher than 0.8, preferably higher than 0.82 and/or mean HS (high sensitivity) circularity higher than 0.89, preferably higher than 0.9.

The term "aspect ratio", as used herein, refers to the ratio of the shortest dimension to the longest dimension of a particle and is in the range of 0 to 1.

The term "high sensitivity (HS) circularity", as used herein, refers to a parameter which is equal to the square of the circularity where the circularity is equal to the ratio of the circumference of a circle equal to the particle's projected area to the actual circumference (perimeter) of a particle. Thus, high sensitivity (HS) circularity is calculated as ($4\pi\times$ Area)/(Perimeter$^2$).

The mean aspect ratio and mean high sensitivity (HS) circularity of the particles can be determined by an optical microscopy based method on a dry dispersion, such as Morphologi G3™ particle size and particle shape analyser (Malvern Instruments). The sample can be prepared by using the Morphologi G3™ integrated dry powder disperser (Malvern Instruments), for example using sample amount of 7 $mm^3$ and dispersion pressure of 1.0 bar. The automated image analysis is suitably performed without filters. The applied magnification depends on the particle size of the analysed powder being typically 10×.

The term "crystalline particles of N—((S)-1-(3-(3-chloro-4-cyanophenyl)-1H-pyrazol-1-yl)-propan-2-yl)-5-(1-hydroxyethyl)-1H-pyrazole-3-carboxamide (I)", as used herein, refers to particles of compound (I) wherein compound (I) is at least partly in crystalline, including microcrystalline, form. For example, the term includes particles of compound (I) wherein compound (I) is at least partly in the crystalline form I, disclosed in WO 2016/120530. The X-ray powder diffraction (XRPD) pattern of crystalline form I has characteristic peaks at about 8.5, 10.4, 16.6, 16.9, and 24.3 degrees 2-theta. Accordingly, the term includes particles which show XRPD characteristic peaks at about 8.5, 10.4, 16.6, 16.9, and 24.3 degrees 2-theta.

The particle size distribution of crystalline particles of compound (I) can be analyzed by laser light diffraction, for example using Beckman Coulter LS13320 laser diffraction particle size analyzer equipped with Tornado Dry Powder System using air as dispersion medium with measurement pressure 24"$H_2O$±2"$H_2O$, sample amount 10 ml, system controlled target 5% for obscuration and applying Fraunhofer optical model.

The parameters considered are the volumetric diameters in μm of the $10^{th}$, $50^{th}$ and $90^{th}$ percentiles of the particles, expressed as Dv10, Dv50 and Dv90 respectively, which are determined by assuming that the particles have a geometric shape equivalent to a sphere.

The specific surface area (SSA) of crystalline particles of compound (I) can be analyzed using the three-point nitrogen adsorption technique based on the Brunauer, Emmett and Teller (BET) theory, for example using TriStar 3000 automated gas adsorption analyzer, (Micromeritics, Inc.). The samples are suitably vacuum dried for 20 hours at 40° C. The volumetric method can be used at the relative pressure range of 0.1-0.3 $P/P_0$.

The present invention provides a method for preparing crystalline particles of N—((S)-1-(3-(3-chloro-4-cyanophenyl)-1H-pyrazol-1-yl)-propan-2-yl)-5-(1-hydroxyethyl)-1H-pyrazole-3-carboxamide (I), the method comprising the steps of a) providing N—((S)-1-(3-(3-chloro-4-cyanophenyl)-1H-pyrazol-1-yl)-propan-2-yl)-5-(1-hydroxyethyl)-1H-pyrazole-3-carboxamide (I) in a solvent which comprises ethanol and water, wherein the amount of water is 35-60%, preferably 40-58%, more preferably 42-55%, per weight of the solvent;

b) heating the mixture to about refluxing temperature until N—((S)-1-(3-(3-chloro-4-cyanophenyl)-1H-pyrazol-1-yl)-propan-2-yl)-5-(1-hydroxyethyl)-1H-pyrazole-3-carboxamide (I) has dissolved;

c) cooling the mixture to about 20-35° C. during at least 3 hours, preferably during about 4 to about 8 hours, optionally with seeding;

d) adding, optionally simultaneously with step c), water during at least 1 hour, preferably during about 2 to about 10 hours, such that after step d) the amount of water in the solvent is 55-80%, preferably 58-78%, more preferably 60-75%, per weight of said solvent; and e) isolating the precipitate.

The solvent to be used in step a) generally comprises ethanol and water. The amount of water in the solvent of step a) is about 35-60%, preferably 40-58%, more preferably 42-55%, per weight of the solvent. Preferably, the solvent consists essentially of ethanol and water. For example, the solvent of step a) contains 35-60% of water and 40-65% of ethanol, preferably 40-58% of water and 42-60% of ethanol, more preferably 42-55% of water and 45-58% of ethanol, per weight of the solvent. According to one embodiment, the solvent of step a) contains 45-52% of water and 48-55% of ethanol, per weight of the solvent. According to another embodiment, the solvent of step a) contains 48-55% of water and 45-52% of ethanol, per weight of the solvent.

The amount of compound (I) used in step a) is suitably about 1-20%, preferably about 5-15%, for example 6-12%, per weight of the solvent. For example, 150-250 kg of compound (I) is provided in 1500-3800 kg of ethanol-water solvent in a suitable reactor. The mixture is then heated with stirring, suitably to about refluxing temperature, for example to about 65-85° C., until compound (I) has been dissolved.

In step c) the mixture is then cooled slowly to 20-35° C. while stirring mildly, typically with stirring speed less than 80 rpm. The cooling is carried out during at least 3 hours, preferably during about 4 to about 8 hours, optionally with seeding using crystals of compound (I). The seeding is suitably carried out at a temperature starting from about 75° C. and optionally again at lower temperatures. For example, the seeding can be carried out once or several times when the temperature of the mixture is about 50-70° C. The amount of seeding crystals is typically less than 0.5% per weight of the compound (I) initially provided to the reactor. The seeding crystals of compound (I) can be prepared, for example, using the method described in WO 2016/120530.

In step d) more water is added slowly to the mixture such that after the water addition the amount of water in the solvent is 55-80%, preferably 58-78%, more preferably 60-75%, per weight of the solvent. Preferably, the solvent consists essentially of ethanol and water. For example, the solvent after step d) contains 55-80% of water and 20-45% of ethanol, preferably 58-78% of water and 22-42% of ethanol, more preferably 60-75% of water and 25-40% of ethanol, per weight of the solvent.

According to one embodiment, the solvent after step d) contains 60-65% of water and 35-40% of ethanol, per weight of the solvent. According to another embodiment, the solvent after step d) contains 65-70% of water and 30-35% of ethanol, per weight of the solvent. According to still another embodiment, the solvent after step d) contains 70-75% of water and 25-30% of ethanol, per weight of the solvent.

According to another embodiment, the solvent of step a) contains 48-55% of water and 45-52% of ethanol, per weight of the solvent, and after step d) 60-65% of water and 35-40% of ethanol, per weight of the solvent. According to another embodiment, the solvent of step a) contains 45-52% of water and 48-55% of ethanol, per weight of the solvent, and in step d) 70-75% of water and 25-30% of ethanol, per weight of the solvent.

The addition of water is carried out during at least 1 hour, preferably during about 2 to about 10 hours, for example during about 6 to about 10 hours. The mixture is stirred mildly during water addition, typically with stirring speed less than 80 rpm. The temperature of the mixture is suitably kept within about 20-35° C. during the addition of water.

Alternatively, steps c) and d) can be carried out simultaneously. In this embodiment water is added during the cooling step. The procedure of water addition can be carried out as explained above while cooling the mixture to about 20-35° C. including the optional seeding. The simultaneous cooling and water addition is suitably carried out during at least 3 hours, preferably during 4-10 hours.

After step d) the mixture can be cooled further, preferably to about 10-30° C., for example to 10-20° C., during at least 1 hour, for example during 1-3 h. After the cooling the mixture is suitably stirred until the precipitation is complete. The precipitated crystalline particles are easy to isolate, for example by centrifuging followed by washing with water and/or ethanol. The isolated precipitate can be dried under reduced pressure, for example at vacuum, at a temperature which is at least 30° C., for example 40-60° C., for a period needed to complete the drying.

The particles obtained by the above method are crystalline, have typically rounded particle shape and exhibit specific surface area (SSA) typically in the range from about 8 to about 16 m²/g, more typically from about 10 to about 15 m²/g. The particles obtained have generally volume median diameter (Dv50) between 100-1000 µm, preferably between 120-800 µm, more preferably between 150-750 µm, in particular between 180-700 µm, for example between 200-650 µm. Dv10 is generally greater than about 50 µm, preferably greater than about 60 µm, more preferably greater than about 70 µm, in particular between 80-500 µm, for example between 100-400 µm. Dv90 is generally lower than 2000 µm, preferably lower than 1500 µm, more preferably lower than 1400 µm, in particular between 300-1300 µm, for example between 400-1200 µm.

Moreover, 80 vol-% of the particles is generally between 50-2000 µm, preferably between 60-1500 µm, more preferably between 70-1400 µm, in particular between 80-1300 µm, for example between 100-1200 µm.

The rounded particles obtained by the above method are typically characterized by mean aspect ratio higher than 0.8 and/or mean high sensitivity (HS) circularity higher than 0.89. More typically, the rounded particles are characterized by mean aspect ratio higher than 0.8 and mean high sensitivity (HS) circularity higher than 0.89. Still more typically, the rounded particles are characterized by mean aspect ratio higher than 0.82 and mean high sensitivity (HS) circularity higher than 0.9.

As the particles obtained by the above method have large volume median diameter, narrow particle size distribution and rounded particle shape characterized by substantial lack of sharp edges, they are easy to isolate, free flowing and exhibit reduced stickiness. The specific surface area (SSA) of the rounded particles obtained by the above method is in the range from about 8 to about 16 m²/g, preferably from about 10 to about 15 m²/g, and does not significantly change even though the volume median diameter (Dv50) of the particles is reduced, for example, to the range of 10-100 µm by milling or other suitable means. This ascertains consistent bioavailability regardless of the variability in particle size. Therefore, if higher homogenity of the tableting mass if desired, the rounded particles can be milled to the particle size having Dv50, for example, in the range of 10-100 µm, preferably between 15-95 µm, typically between 20-90 µm, such particles being well suited in the preparation pharmaceutical dosage forms for oral administration such as tablets.

The crystalline rounded particles of compound (I) obtained by the method of the invention can therefore be used as such or in milled form in the preparation of pharmaceutical dosage forms, such as tablets, capsules or powders together with excipients which are known in the art.

The invention is further illustrated by the following examples.

Example 1. Preparation of Crystalline Particles of N—((S)-1-(3-(3-Chloro-4-cyano-phenyl)-1H-pyrazol-1-yl)propan-2-yl)-5-(1-hydroxyethyl)-1H-pyrazole-3-carboxamide (I)

Granular sodium borohydride (15 kg) and EtOH (1370 kg) were placed into the 6.3 m³ enamel reaction vessel. The mixture was solubilized by stirring for 30 min at 22° C. (S)-3-acetyl-N-(1-(3-(3-chloro-4-cyano-phenyl)-1H-pyrazol-1-yl)propan-2-yl)-1H-pyrazole-5-carboxamide (225 kg) was added to the reaction vessel. The mixture was then stirred at 22° C. for 4 hours to complete the reaction. Then pH of the mixture was adjusted to acidic with HCl in water. Water (800 kg) was then added and the pH of the mixture was set to 7.0±1.0 by addition of NaOH in water. The mixture was warmed to 65° C. and then transferred to 6.3 m³ jacketed steel reaction vessel. The mixture was warmed to 78° C. to dissolve the mixture. The solution was cooled to 64° C. under nitrogen atmosphere. The solution was seeded at 64° C. under mild stirring. The solution was then cooled during 8 h to 30° C. under mild stirring. Thereafter water (2600 kg) was added during 7-10 h at 30° C. under mild stirring. The mixture was cooled during 2 h to 20° C. under mild stirring and then stirred further for 1 h. The precipitated product was isolated by centrifuge, washed with water and dried under vacuum at 40-60° C. to obtain 214 kg of crystalline particles with rounded particle shape.

Example 2. Preparation of Crystalline Particles of N—((S)-1-(3-(3-Chloro-4-cyano-phenyl)-1H-pyrazol-1-yl)propan-2-yl)-5-(1-hydroxyethyl)-1H-pyrazole-3-carboxamide (I)

Water (450 kg), EtOH (920 kg) and (N—((S)-1-(3-(3-chloro-4-cyanophenyl)-1H-pyrazol-1-yl)propan-2-yl)-3-(1-hydroxyethyl)-1H-pyrazole-5-carboxamide (215 kg) were placed into the 6.3 m³ steel reaction vessel with 100 kg of rinse EtOH. The mixture was dissolved by warming to 75° C. Activated carbon SX Ultra (11 kg) and Celite (21 kg) were added followed by stirring at 78° C. for 1 h. The mixture was cooled to 75° C. under nitrogen atmosphere and filtered. The filtrate was transferred into 6.3 m³ jacketed steel reaction vessel. The carbonlcelite cake was washed with a warmed (75° C.) mixture of water (970 kg) and EtOH (345 kg). The washing liquid was also added to the reaction vessel. The solution was stirred at 78° C. for 30 min and then cooled to 70° C. Mild stirring was maintained during the rest of the process. The solution was seeded at 70° C. and then cooled during 4 h to 30±5° C. Thereafter water (840 kg) was added during 6 h at 30±5° C. The mixture was cooled during 2 h to 20° C. and then stirred further for 1 h. The precipitated product was isolated by centrifuge, washed with EtOH and dried under vacuum at 40-60° C. to obtain 190 kg of crystalline particles with rounded particle shape.

Example 3. Preparation of Crystalline Particles of N—((S)-1-(3-(3-Chloro-4-cyano-phenyl)-1H-pyrazol-1-yl)propan-2-yl)-5-(1-hydroxyethyl)-1H-pyrazole-3-carboxamide (I)

Water (1400 kg), EtOH (1215 kg) and (N—((S)-1-(3-(3-chloro-4-cyanophenyl)-1H-pyrazol-1-yl)propan-2-yl)-3-(1-hydroxyethyl)-1H-pyrazole-5-carboxamide (210 kg) were placed into the 6.3 m³ steel reaction vessel. The mixture was dissolved by warming to 75° C. Activated carbon SX Ultra (11 kg) and Celite (21 kg) were added followed by stirring for 1 h. The mixture was then filtered as hot. The filtrate was transferred into 6.3 m³ jacketed steel reaction vessel. The carbonlcelite cake was washed with EtOH (170 kg). The washing liquid was also added to the reaction vessel. Temperature was adjusted to 70° C. The solution was seeded at 70° C. and then cooled to 60° C. Then the mixture cooled to 30° C. in 4 hours and water (1050 kg) was added simultaneously. The mixture was stirred further for 30 minutes. The precipitated product was isolated by centrifuge, washed with water and dried under vacuum at 70° C. to obtain 190 kg of crystalline particles with rounded particle shape.

Example 4. Determination of Particle Size Distribution

The particle size distribution of the crystalline rounded particles of compound (I) prepared according to the present invention was determined by laser light diffraction. The determination was carried out by using Beckman Coulter LS13320 laser diffraction particle size analyzer equipped with Tornado Dry Powder System using air as dispersion medium with measurement pressure 24"$H_2O$±2"$H_2O$, sample amount 10 ml, system controlled target 5% for obscuration and applying Fraunhofer optical model. The results of the particle size analysis are shown in FIG. 1. According to the analysis, Dv10 value of the particles is 359 µm, Dv50 is 632 µm and Dv90 is 925 µm.

Figure 2:
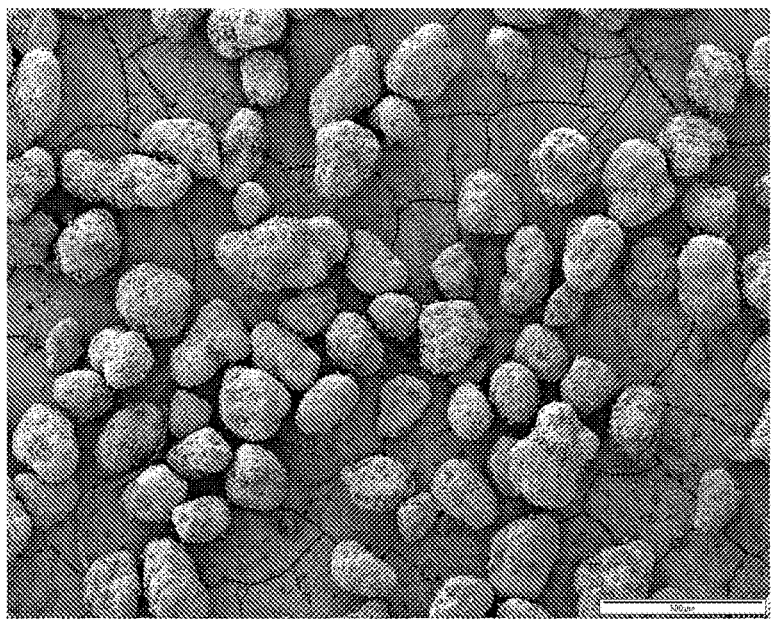
FIG. 2 shows a scanning electron microscope image (50 fold magnification, bar 500 μm) of crystalline particles of compound (I) prepared according to the present invention.
Figure 3:
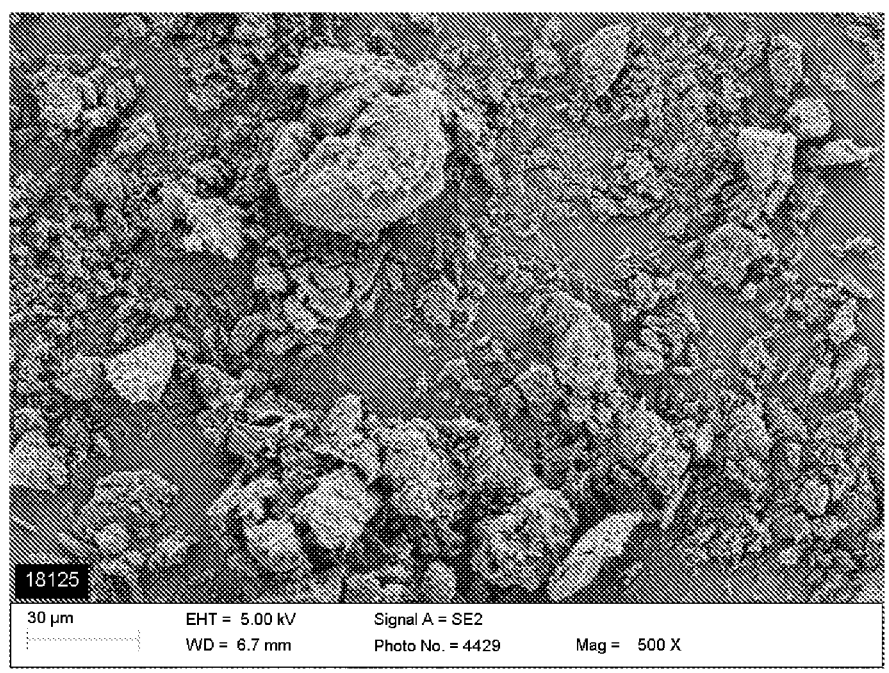
FIG. 3 (reference) shows a scanning electron microscope image (500 fold magnification) of particles of compound (I) prepared according to Example 1 of WO 2016/120530.

Example 5. Characterization of Particles by Scanning Electron Microscope (SEM) Images Crystalline rounded particles of compound (I) prepared according to the present invention were characterized by scanning electron microscope imaging. The SEM figure is shown in FIG. 2 (50 fold magnification, bar 500 µm). As a comparison, a SEM image of the particles prepared according to Example 1 of WO 2016/120530 is shown in FIG. 3 (500 fold magnification, bar 30 µm). The particles prepared according to the present invention exhibit rounded particle shape with narrow particle size distribution while the particles prepared according to WO 2016/120530 are small and irregular with sharp edges.

Example 6. Determination of Specific Surface Area (SSA) of Particles

The specific surface area (SSA) and particle size distribution (PSD) were determined for two batches (A and B) of crystalline rounded particles of compound (I) prepared according to the present invention. The particles of the two batches were then milled followed by the determination of SSA and PSD. The results are shown in Tables 1 and 2. The results show that the specific surface area (SSA) of the particles did not significantly change even if the particles were milled to reduced particle size.

TABLE 1

| Batch | SSA ($m^2/g$) | Volume particle size, Dv10 (µm) | Volume particle size, Dv50 (µm) | Volume particle size, Dv90 (µm) |
|---|---|---|---|---|
| A (unmilled) | 13 | 171 | 407 | 625 |
| A (milled) | 14 | 2 | 36 | 218 |

TABLE 2

| Batch | Specific surface area ($m^2/g$) | Volume particle size, Dv10 (µm) | Volume particle size, Dv50 (µm) | Volume particle size, Dv90 (µm) |
|---|---|---|---|---|
| B (unmilled) | 12 | 176 | 389 | 826 |
| B (milled) | 13 | 3 | 96 | 292 |

The specific surface area was measured using the three-point nitrogen adsorption technique based on the Brunauer, Emmett and Teller (BET) theory using TriStar 3000 automated gas adsorption analyzer (Micromeritics, Inc.). The samples were vacuum dried for 20 hours in 40° C. The volumetric method was applied at the relative pressure range 0.1-0.3 $P/P_0$.

The invention claimed is:

1. Crystalline particles of N—((S)-1-(3-(3-chloro-4-cyano-phenyl)-1H-pyrazol-1-yl)-propan-2-yl)-5-(1-hydroxyethyl)-1H-pyrazole-3-carboxamide (I) having a specific surface area (SSA) in a range from about 8 to about 16 $m^2/g$.

2. The crystalline particles according to claim 1 having a volume median diameter (Dv50)≥10 µm.

3. The crystalline particles according to claim 1 having a volume median diameter (Dv50) ranging from between 10 µm and 1000 µm.

4. The crystalline particles according to claim 1 having a volume median diameter (Dv50) ranging from between 100 µm and 1000 µm.

5. The crystalline particles according to claim 4, wherein the particles have a rounded particle shape.

6. The crystalline particles according to claim 5 characterized by a mean aspect ratio higher than 0.8, and/or a mean high sensitivity (HS) circularity higher than 0.89.

7. The crystalline particles according to claim 6 characterized by a mean aspect ratio higher than 0.8 and a mean high sensitivity (HS) circularity higher than 0.89.

8. The crystalline particles according to claim 7 characterized by a mean aspect ratio higher than 0.82 and a mean high sensitivity (HS) circularity higher than 0.9.

9. The crystalline particles according to claim 1 having a volume median diameter (Dv50) ranging from between 10 µm and 100 µm.

10. Crystalline particles of N—((S)-1-(3-(3-chloro-4-cyanophenyl)-1H-pyrazol-1-yl)-propan-2-yl)-5-(1-hydroxyethyl)-1H-pyrazole-3-carboxamide (I) having a rounded particle shape and a volume median diameter (Dv50) ranging from between 100 µm and 1000 µm.

11. A pharmaceutical dosage form comprising N—((S)-1-(3-(3-chloro-4-cyanophenyl)-1H-pyrazol-1-yl)-propan-2-yl)-5-(1-hydroxyethyl)-1H-pyrazole-3-carboxamide (I) as an active ingredient, wherein the active ingredient is in the form of the crystalline particles according to claim 1.

12. A pharmaceutical dosage form comprising N—((S)-1-(3-(3-chloro-4-cyanophenyl)-1H-pyrazol-1-yl)-propan-2-yl)-5-(1-hydroxyethyl)-1H-pyrazole-3-carboxamide (I) as an active ingredient, wherein the active ingredient is prepared from the crystalline particles according to claim 10.

13. The pharmaceutical dosage form according to claim 12, wherein the crystalline particles are milled to provide a volume median diameter (Dv50) ranging from between 10 µm and 100 µm.

14. The crystalline particles according to claim 1, wherein the specific surface area (SSA) is analyzed using a three-point nitrogen adsorption technique based on the Brunauer, Emmett and Teller (BET) theory.

15. The crystalline particles according to claim 6, wherein the mean aspect ratio and/or mean high sensitivity (HS) circularity is determined by an optical microscopy method on a dry powder dispersion.

16. The crystalline particles according to claim 2, wherein the volume median diameter (Dv50) is measured by laser light diffraction using air as dispersion medium and applying Fraunhofer optical model.

17. A method for preparing crystalline particles of N—((S)-1-(3-(3-chloro-4-cyanophenyl)-1H-pyrazol-1-yl)-propan-2-yl)-5-(1-hydroxy-ethyl)-1H-pyrazole-3-carboxamide (I) according to claim 1:
  a) providing N—((S)-1-(3-(3-chloro-4-cyanophenyl)-1H-pyrazol-1-yl)-propan-2-yl)-5-(1-hydroxyethyl)-1H-pyrazole-3-carboxamide (I) in a solvent which comprises ethanol and water, wherein the amount of water is 35-60%, per weight of the solvent;
  b) heating the mixture to about refluxing temperature until N—((S)-1-(3-(3-chloro-4-cyanophenyl)-1H-pyrazol-1-yl)-propan-2-yl)-5-(1-hydroxyethyl)-1H-pyrazole-3-carboxamide (I) has dissolved;
  c) cooling the mixture to about 20-35° C. during at least 3 hours, optionally with seeding;
  d) adding, optionally simultaneously with step c), water during at least 1 hour, such that after step d) the amount of water in the solvent is 55-80% per weight of said solvent; and
  e) isolating the precipitate.

18. The method according to claim 17, wherein the particles have a volume median diameter (Dv50) ranging from between 100 μm and 1000 μm.

19. The method according to claim 17, wherein the particles have a rounded particle shape.

20. The method according to claim 17, wherein the particles have a specific surface area (SSA) in a range from about 8 to about 16 m$^2$/g.

21. The method according to claim 17, wherein in step a) the solvent consists essentially of ethanol and water.

22. The method according to claim 21, wherein in step a) the solvent contains 35-60% of water and 40-65% of ethanol per weight of the solvent.

23. The method according to claim 17, wherein in step d) the temperature of the mixture is kept within about 20-35° C. during the addition of water.

24. The method according to claim 17, wherein steps c) and d) are carried out simultaneously.

25. The method according to claim 17, wherein after step d) the mixture is cooled further to about 10-30° C. for at least 1 hour.

26. The method according to claim 17, wherein during step c) the mixture is seeded at about 50-70° C.

27. The method according to claim 17, wherein the amount of compound (I) in step a) is about 1-20% per weight of the solvent.

28. The method according to claim 17, wherein the isolated precipitate is dried under reduced pressure at a temperature of at least 30° C.

29. The method according to claim 28, wherein the isolated precipitate is dried under reduced pressure at 40-60° C.

* * * * *